United States Patent [19]

Ginsburg et al.

[11] Patent Number: 4,789,234

[45] Date of Patent: Dec. 6, 1988

[54] APPARATUS AND METHOD FOR TESTING THE MOTION CONTRAST VISUAL SENSITIVITY OF AN INDIVIDUAL

[75] Inventors: Arthur P. Ginsburg; David A. Ginsburg; Robert P. Ginsburg, all of Dayton, Ohio

[73] Assignee: Vistech Consultants, Inc., Beavercreek, Ohio

[21] Appl. No.: 254

[22] Filed: Jan. 2, 1987

[51] Int. Cl.⁴ .............................................. A61B 3/02
[52] U.S. Cl. ..................................... 351/239; 351/246; 351/245; 351/238
[58] Field of Search ................ 351/211, 233, 234, 235, 351/243, 245, 239, 246, 238

[56] References Cited

U.S. PATENT DOCUMENTS

| | | | |
|---|---|---|---|
| 2,000,153 | 5/1935 | Watson | 40/52 |
| 3,524,702 | 8/1970 | Bellows et al. | 351/211 |
| 3,807,839 | 4/1974 | Sugarman et al. | 351/243 |
| 4,493,539 | 1/1985 | Cannon, Jr. | 351/205 |
| 4,511,228 | 4/1985 | Von Gierke et al. | 351/243 |
| 4,526,452 | 7/1985 | Hirsch | 351/243 |
| 4,550,990 | 11/1985 | Trispel et al. | 351/243 |

Primary Examiner—Rodney B. Bovernick
Assistant Examiner—Jay Ryan
Attorney, Agent, or Firm—Biebel, French & Nauman

[57] ABSTRACT

The motion contrast visual sensitivity of an individual is tested by means of a target having thereon patches each composed of alternating light and dark bars, with individual patches varying in contrast and spatial frequency, and also in orientation. The target is viewed by way of a slot through a housing positioned in front of the individual under test, and a shutter rotating within the housing at a controlled speed periodically blocks the slot at a rate sufficiently slow, e.g. 30 cycles per second, for the observer to detect the resulting conditions of flicker.

12 Claims, 2 Drawing Sheets

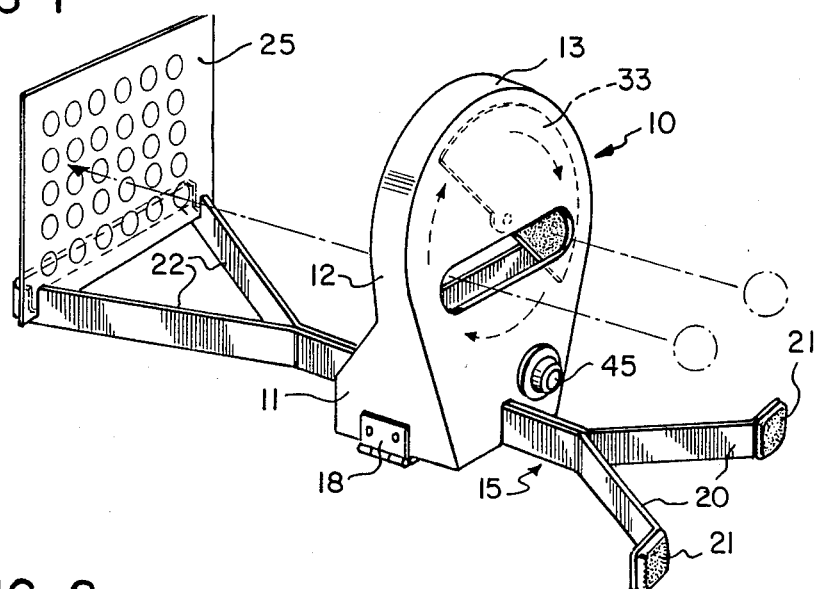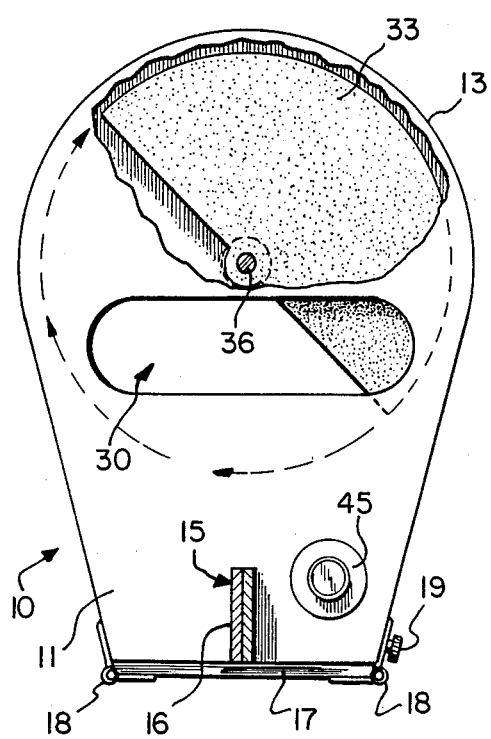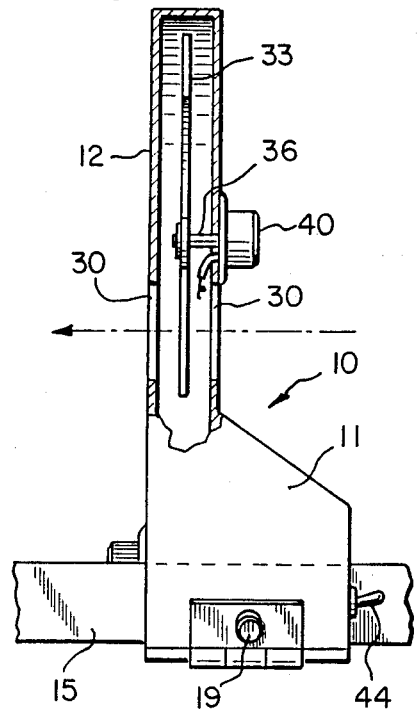

4,789,234

APPARATUS AND METHOD FOR TESTING THE MOTION CONTRAST VISUAL SENSITIVITY OF AN INDIVIDUAL

BACKGROUND OF THE INVENTION

Ginsburg U.S. Pat. No. 4,365,873 discloses a technique for testing the visual sensitivity of an individual in terms of contrast sensitivity and spatial frequency response in conjunction with a chart having thereon a multiplicity of grating patches which vary in contrast, spatial frequency and angular orientation. In use, the chart is scanned beginning with the patches of maximum contrast and minimum frequency until the low contrast level or the high spatial frequency prevents the observer from detecting the gratings or their orientation. The threshold levels of the individual under test are quantified and compared to a norm.

SUMMARY OF THE INVENTION

The present invention is concerned with testing the motion contrast sensitivity of individuals, and more specifically the testing of the motion cells in the visual system of an individual. In a specific example of the invention, motion contrast sensitivity is tested by utilizing the principles and chart such as is disclosed in the above Ginsburg patent under conditions wherein an apparent flickering movement is imparted to the chart with respect to the viewing position, by causing flickering movement of the chart itself or by flickering the observer's view of the chart, as by alternately blocking and unblocking the observer's line of sight to the chart or by flickering the illumination of the chart and hence the observer's view thereof.

One objective of the present invention is to provide apparatus and a method for testing the visual acuity of an observer under test conditions controlled to cause apparent flickering movement of a target such as a chart of the type disclosed in the above Ginsburg patent.

A more specific object of the invention is to provide motion contrast sensitivity testing apparatus which is so constructed and arranged that a chart of the type disclosed in the Ginsburg patent is observed by the individual being tested under conditions of controlled flickering illumination.

Specific apparatus and method steps by which the objectives of the invention are accomplished are described hereinafter in connection with the drawings.

BRIEF DESCRIPTION OF THE DRAWINGS

FIG. 1 is a somewhat diagrammatic view in perspective illustrating the general construction and use of testing apparatus in accordance with the invention;

FIG. 2 is a front elevational view of the major component of the apparatus in FIG. 1;

FIG. 3 is a side view, partially in section on line 3—3 of FIG. 2;

DESCRIPTION OF THE PREFERRED EMBODIMENT

Figure 4:
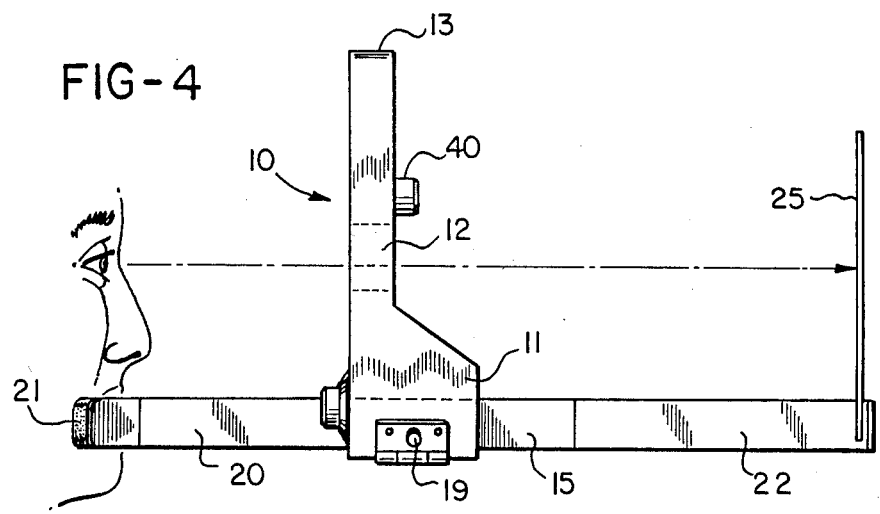
FIG. 4 is a side elevational view further illustrating the manner of use of the apparatus of the invention.

The major component of the testing apparatus of the invention is a housing indicated generally at 10, which may be mounted on a stand for use but which normally will be held by the individual under test. The housing 10 has a base section 11 and an upper portion 12 which is relatively narrow from front to back as compared with the base section 11, and which includes a semi-cylindrical top portion 13.

A positioning member 15 having the general shape of a double-ended Y fits in a slot 16 in the bottom of housing 10 and is retained therein by the housing bottom cover 17, which is hinged at 18 to one side of the housing and releasably secured to the other side of the housing by any suitable latch means, shown as a second hinge 18 and a thumb screw 19. At its end in front of housing 10, the positioning member 15 includes a pair of arms 20 having pads 21 on their ends for engagement by the cheeks of the observer to position the observer's head in proper viewing relation with the remainder of the apparatus. The other end of the positioning member 15 projects beyond the back of housing 10 and has a second pair of arms 22 which are slotted or otherwise configured at their outer end to receive and support a target 25, which preferably is a chart of the characteristics described in the above Ginsburg patent.

Figure 5:
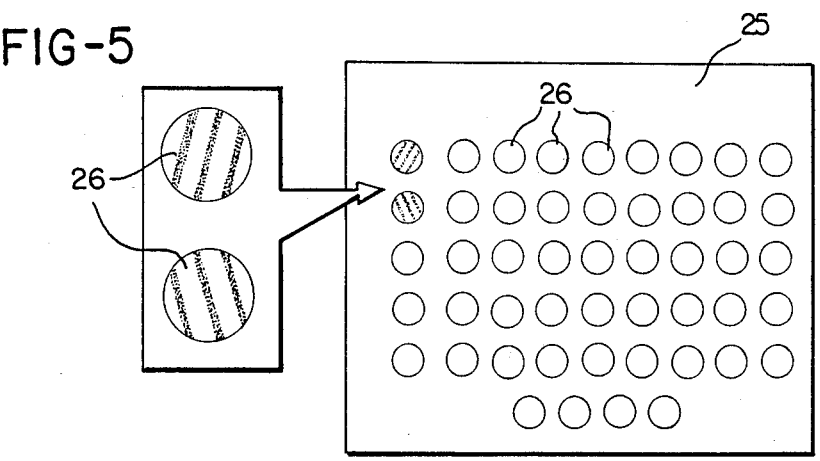
FIG. 5 is a somewhat diagrammatic view illustrating a typical target chart used with the apparatus of the invention.

Referring to FIG. 5, a typical such chart 25 is a rectangular card having thereon a series of rows of patches 26 which vary in contrast over a substantial range. As shown, each patch comprises parallel monochromatic (gray) bars on a white background, with the gray varying in value from dark to light along each row to provide the desired progressive variation in density. In addition, the patches in each row also differ in spatial frequency from the patches in the other rows, and selected patches have the bars therein at a different orientation with respect to the vertical from the bars in other patches in the row to facilitate checking the tested person's ability to detect specific patches. Thus as shown in the Ginsburg patent, the bars in some patches may extend vertically while those in other patches are inclined to the right or left from the vertical.

A slot 30 extends most of the way across both the front and back walls of the upper portion 12 of the housing at an appropriate level such that when the cheeks of an observer rest against the pads 21, the observer's field of view through the slots 30 will be centered on the chart 25. Inside the upper portion of the housing is a semi-circular disk 33 mounted on the drive shaft 36 of an electric motor 40 which is in turn mounted on one of the housing walls, shown as the rear wall. The size and proportions of the disk 33 are such that when it is in its bottom limit position with its straight side horizontal, it will completely block the slots 30, and when it is in its corresponding upper limit position, it will be entirely removed from the line of the sight through the slots 30.

The motor 40 may be powered by house current, especially if the housing 10 is mounted on a fixed stand. For total portability of the apparatus, however, the motor 40 is preferably powered by one or more batteries mounted within the lower portion 11 of the housing 10, preferably in a position for ready access for replacement when the bottom cover 15 is opened. An On-Off switch 44 for the motor is shown as mounted on the back of the lower part of the housing, and a knob 45 on the front of the housing operates through conventional circuitry to regulate the speed of motor 40.

In use, the testing of an individual's visual acuity is carried out in substantially the same manner as described in the Ginsburg patent, under conditions of flicker established by the alternate opening and closing of the line of sight through the slits 30 by rotation of the disk 33, which simulates movement of the chart itself while the patches thereon are being observed. The rate of flicker must be retained within the range which the human eye can detect, which is usually not faster than 30 cycles per second, and this rate can be varied, by the knob 45 in accordance with this ability of each particular individual.

More specifically, the testing is carried out by having the observer scan each line of patches beginning with those of maximum contrast and minimum frequency until the low contrast level or the high spatial frequency prevents that individual from detecting the flickering gratings or their orientation. The threshold levels of each individual established in this manner are quantified and compared with the results obtained by similar testing under conditions of steady illumination of the target.

For optimum testing conditions and results, the face of the disk 33 on the observer's side is painted the average gray of the grating patches on the chart 25. In this manner, the mean luminance of the gratings is maintained essentially constant, thereby maintaining mean retinal adaptation on the part of the individual under test.

While the method herein described, and the form of apparatus for carrying this method into effect constitute preferred embodiments of this invention, it is to be understood that the invention is not limited to this precise method and form of apparatus, and that changes may be made in either without departing from the scope of the invention which is defined in the appended claims.

What is claimed is:

1. Apparatus for testing subjectively the visual motion contrast sensitivity of an individual, comprising:
   (a) means for presenting a series of targets at a predetermined location,
   (b) means establishing a viewing position for an individual to be tested having a limited line of sight to said target location,
   (c) each of said targets consisting of light and dark areas with said dark areas on each said target being of the same value but differing in value from said dark areas on other said targets to provide said targets with correspondingly different levels of contrast, and
   (d) means for selectively blocking and unblocking said line of sight at a rate which will cause the human eye to detect flicker, and thereby promoting determination of the levels of contrast in said targets which are detected by the individual at said viewing position under such conditions of flicker.

2. Apparatus as defined in claim 1 wherein said last named means comprises means defining a shutter, and means for moving said shutter alternately into and out of said line of sight.

3. Apparatus as defined in claim 2 wherein said targets are essentially monochromatic, and the surface of said shutter facing said viewing position is of the same color as said targets and of color value corresponding to the mean color value of said targets.

4. Apparatus for testing the visual motion contrast sensitivity of an individual, comprising
   (a) a housing having a viewing opening therethrough,
   (b) means projecting from one side of said housing for holding a target having thereon alternating light and dark areas arranged for testing the visual contrast sensitivity of an observer,
   (c) means projecting from the other side of said housing for establishing a viewing position from which an observer can view said target only through said viewing opening, and
   (d) means for imparting to said target an apparent flickering movement with respect to said viewing position.

5. Apparatus as defined in claim 3 wherein said imparting means comprises means in said housing for alternately blocking and unblocking said viewing opening at a rate within the ability of the human eye to detect flicker.

6. Apparatus as defined in claim 4 wherein said last named means comprises a shutter mounted for rotational movement in said housing across said viewing opening, said shutter being so proportioned as to block said opening completely in one rotational position thereof and to open said viewing opening completely in the opposite rotational position thereof, and means in said housing for rotating said shutter at a rate within the ability of the human eye to detect flicker.

7. Apparatus as defined in claim 6 wherein said areas on said target comprise gray bars on a white background, said gray bars vary in value from dark to light, the surface of said shutter facing said viewing position is of a gray value corresponding to the mean gray value of said bars.

8. Apparatus as defined in claim 4 wherein said last named means comprises a substantially semi-circular shutter mounted in said housing on an axis adjacent said viewing opening for rotation between limit positions wherein said shutter alternately opens and closes said viewing opening, and means for rotating said shutter at a rate within the ability of the human eye to detect flicker.

9. Apparatus as defined in claim 8 wherein said areas on said target comprise gray bars on a white background, said gray bars vary in value from dark to light, the surface of said shutter facing said viewing position is of a gray value corresponding to the mean gray value of said bars.

10. The method of testing the visual motion contrast sensitivity of an individual which comprises the steps of
    (a) locating an eye of an observer to be tested at a predetermined viewing position relative to a target having thereon multiple alternating light and dark areas which vary in contrast and/or spatial frequency,
    (b) imparting to said target an apparent flickering movement with respect to said viewing position, and
    (c) determining the ability of such eye to detect the differences between said flickering target areas.

11. The method defined in claim 10 wherein said flicker imparting step is carried out by intermittently varying the visibility of said target from said viewing position at a rate within the ability of the human eye to detect flicker.

12. The method defined in claim 10 wherein said flicker imparting step is carried out by alternately blocking and unblocking the line of sight between said viewing position and said target at a rate within the ability of the human eye to detect flicker.

* * * * *